United States Patent
Brugel et al.

(10) Patent No.: US 7,026,433 B2
(45) Date of Patent: *Apr. 11, 2006

(54) CONTINUOUS BIOREACTOR PROCESS FOR THE PREPARATION OF POLYESTER CYCLIC OLIGOMERS

(75) Inventors: Edward G. Brugel, Wilmington, DE (US); Robert DiCosimo, Rockland, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 98 days.

This patent is subject to a terminal disclaimer.

(21) Appl. No.: 10/698,275

(22) Filed: Oct. 31, 2003

(65) Prior Publication Data

US 2005/0054809 A1    Mar. 10, 2005

Related U.S. Application Data

(63) Continuation-in-part of application No. 10/426,600, filed on Apr. 30, 2003.

(60) Provisional application No. 60/380,034, filed on May 3, 2002.

(51) Int. Cl.
    C08G 63/78    (2006.01)
    C08F 2/00     (2006.01)
    C08J 1/00     (2006.01)

(52) U.S. Cl. .................. 528/274; 528/308.6; 528/491; 528/493; 528/497; 528/501; 526/67; 526/68; 526/69; 526/70; 526/89; 526/206; 526/208; 526/318.2; 524/732; 524/768; 524/770

(58) Field of Classification Search ................ 528/274, 528/308.6, 491, 493, 497, 501; 526/67, 68, 526/69, 70, 89, 206, 208, 318.2; 524/732, 524/768, 770

See application file for complete search history.

(56) References Cited

U.S. PATENT DOCUMENTS

| 2,020,298 A | 11/1935 | Corothers et al. |
| 5,466,744 A | 11/1995 | Evans et al. |
| 5,661,214 A | 8/1997 | Brunelle |

FOREIGN PATENT DOCUMENTS

WO    WO 93/19058    9/1993

OTHER PUBLICATIONS

Berkane, Christopher, et al., "Lipase-Catalyzed Polyester Synthesis in Organic Medium. Study of Ring-Chain Equilibrium", Macromolecules 1997, 30, p7729-7734.*

Mezoul, Gilles, et al., "Enzyme-catalyzed syntheses of poly (1,6-hexanediyl isophthalate) and poly(1,6-hexanediyl terephthalate) in organic medium", Polymer Bulletins, 36, 541-548 (1996).*

Lavalette, Arnaud et al., "Lipase-Catalyzed Synthesis of a Pure Macrocyclic Polyester from Dimethyl Terephthalate and Diethylene Glycol", BioMacromolecules, vol 3, No. 2, Mar./Apr. 2002.*

(Continued)

Primary Examiner—Samuel A. Acquah

(57) ABSTRACT

A continuous process for the process for the enzyme-catalyzed preparation of cyclic ester oligomers from linear ester oligomers. The process may use a linear or recirculating reactor.

10 Claims, 1 Drawing Sheet

OTHER PUBLICATIONS

Biomacromolecules, Mar./Apr. 2002, Lipase-Catalyzed Synthesis of a Pure Macrocyclic Polyester form Dimethyl Terephthalate and Diethylene Glycol, Arnaud Lavalette et al.,.

Intramolecular Reaction in Polycondensations. I. The Theory of Linear Systems, Journal of chemical Physics, vol. 18, No. 12, Dec. 1950, Homer Jacobson et al.

Macormolecules 1997, 30-7729-7734, Lipase-Catalyzed Polyester Synthesis in Organic Medium. Study of Ring-Chain Equilibrium, Berkane et al,.

2445 Polymer Bulletin 361(1966) May., No. 5, Berlin, DE., Enzyme-Catalyzed Synthesis of Poly(1,6-hexanediylisophthalate) and poly(1,6-hexanediyl terephthalate) in organic medium, Gilles Mezoul.

Kondro R. et al., Lipase-Catalyzed Selective Transformation...Dioxide, Macromolecular Bioscience, Wiley Vch, pp. 267-271.

Berkane C., et al., "Lipase-Catalyzed Polyester..Equilibrium", Berkane, C. et al., pp. 7729-7734.

Patent Abstracts of Japan., JP 2002 017385 A. (Keio Gijuku), Jan. 22, 2002.

Patent Abstracts of Japan, JP 2002 320499, (Keio Gijuku) Jan. 22, 2002.

\* cited by examiner

CONTINUOUS BIOREACTOR PROCESS FOR THE PREPARATION OF POLYESTER CYCLIC OLIGOMERS

CROSS REFERENCE TO RELATED APPLICATIONS

This application is being filed as Continuation of application Ser. No. 10/426,600, filed Apr. 30, 2003, which claims the benefit of the filing date of U.S. Provisional Application No. 60/380,034, filed May 3, 2002.

FIELD OF THE INVENTION

The present invention relates to a continuous process for the enzyme-catalyzed preparation of cyclic ester oligomers from linear ester oligomers.

BACKGROUND OF THE INVENTION

Cyclic ester oligomers (CEOs) have been known for a long time; see for instance U.S. Pat. No. 2,020,298. They are known to be present in varying, usually small, quantities in many linear polyesters and have been isolated from such linear polyesters; see for example A. G. Harrison, "Analysis of cyclic oligomers of poly(ethylene terephthalate) by liquid chromatography/mass spectrometry", *Polymer*, 38(10), 2549–2555 (1997) and G. Wick, H. Zeitler, "Cyclic Oligomers in polyesters from diols and aromatic dicarboxylic acids", *Angewandte Makromolekulare Chemie*, (1983), 112, 59–94. They are often low viscosity liquids, and it has long been known that they may be polymerized to higher molecular weight linear polyesters by ring opening polymerization; see for instance U.S. Pat. Nos. 5,466,744 and 5,661,214 and references cited therein. This ability to readily form a high molecular weight polymer from a relatively low viscosity liquid has made these CEOs attractive as materials for reaction injection molding type processes, wherein a low viscosity material is converted to a high molecular weight polymer in a mold, so that a final shaped part is obtained.

However such CEOs have been difficult and expensive to prepare, for example requiring very high dilution conditions and/or using relatively expensive starting materials such as diacyl halides in conjunction with diols and a base to react with the HCl formed; see for instance U.S. Pat. No. 5,466,744. These high manufacturing costs have in many cases prevented the use of CEOs commercially, and therefore lower cost routes to CEOs are of great interest.

More recently it has been found that polyesters can be made from dicarboxylic acids or their diesters and diols using enzymes that catalyze (trans)esterification; see for instance X. Y. Wu, et al., *Journal of Industrial Microbiology and Biotechnology*, vol. 20, p. 328–332 (1998), E. M. Anderson, et al.; *Biocatalysis and Biotransformation*, vol. 16, p. 181–204 (1998); and H. G. Park, et al., *Biocatalysis*, vol. 11, p. 263–271 (1994). In some instances, in such reactions the production of small amounts of CEO coproducts has also been reported; see for instance G. Mezoul, et al., *Polymer Bulletin*, vol. 36, p. 541–548 (1996). There has also been a study reported on the amounts of CEOs that should be present in such reactions; see C. Berkane, et al., *Macromolecules*, vol. 30, p. 7729–7734 (1997). The latter study concluded that formation of the CEOs in the enzyme catalyzed reactions followed the same type of rules that govern the formation of these CEOs in nonenzymatic catalyzed reactions, and that only small fractions of CEOs should be produced in such enzymatic reactions unless they were done under very dilute conditions. In the processes described in all of these references the byproduct alcohol or water from the transesterification/esterification was removed (usually by sparging with an inert gas) to drive the polymeric product to higher molecular weight.

A recent paper, A. Lavalette, et al., *Biomacromolecules*, vol. 3, p. 225–228 (2002), describes a process whereby an enzymatically catalyzed reaction of dimethyl terephthalate and diethylene glycol or bis(2-hydroxyethyl)thioether leads to essentially complete formation of the dimeric cyclic ester, while use of 1,5-pentanediol leads to a relatively high yield of the dimeric cyclic ester, along with some linear polyester. The formation of high yields of the cyclic ester with diethylene glycol and bis(2-hydroxyethyl)thioether is attributed to a π-stacking-type short range interaction which favored formation of the dimeric cyclic ester.

Heretofore, however, it has been unknown in the art how to produce CEOs from the reaction of dicarboxylic acids with diols in a continuous process to obtain the CEOs in an amount that is greater than that predicted by thermodynamic equilibrium, as taught by H. Jacobson and W. H. Stockmeyer in "Intermolecular Reaction and Polycondensation I. The Theory of Linear Systems", *The Journal of Chemical Physics*, Vol. 18 Number 12, December 1950, and which is well-known to persons skilled in the art.

Surprisingly, it has been found that when linear ester oligomers (LEO'S) are reacted in the presence of an esterification/transesterification enzyme catalyst in a non-aqueous medium using the continuous process of the present invention, significant quantities of cyclic ester oligomer can be obtained.

SUMMARY OF THE INVENTION

There is disclosed and claimed herein a process for the production of cyclic ester oligomers, comprising carrying out in a continuous manner the steps of:
(i) contacting linear ester oligomers dissolved in a solvent with an enzyme to generate a solution enriched in cyclic ester oligomers, and
(ii) separating the cyclic ester oligomers from the solution.

The process may be conducted in a either a recirculating or linear reactor.

DETAILED DESCRIPTION OF THE INVENTION

Figure 1:
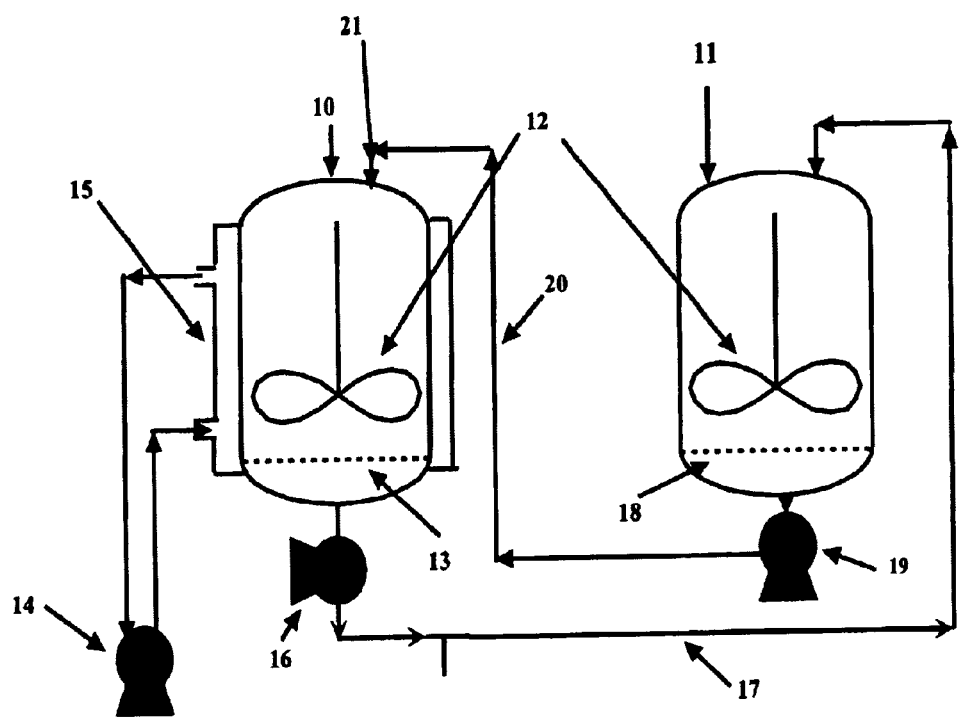
FIG. 1 is a schematic diagram of the reactor used in the continuous process described in the Example.

Herein certain terms are used and some of them are defined below:

By "degree of polymerization" (DP) is meant the number of repeat units in an oligomer chain. By a repeat unit of the polyester of a dicarboxylic acid and a diol is meant a unit having one dicarboxylic acid derived unit and one diol derived unit. A repeat unit for a hydroxycarboxylic acid is derived from a single hydroxycarboxylic acid molecule.

As used herein, the term "dicarboxylic acid" means an organic compound that has two carboxyl groups and includes those compounds that are derived from a dicarboxylic acid or a simple derivative thereof such as a diester, or a half-acid ester of the dicarboxylic acid, or mixtures thereof. The dicarboxylic acid may be substituted with one or more functional groups such as alkyl, halogen, ether, thioether, and oxo (keto) that do not substantially interfere with the various reactions described in the processes herein. The dicarboxylic acid may include an aromatic ring as part of its structure. An aliphatic dicarboxylic acid may also be used. The term "hydroxycarboxylic acid" means an organic compound that has a hydroxy group and a carboxyl group and includes those compounds whose carboxyl group is a carboxylic acid or simple derivative thereof such as an ester.

By a "diol" is meant an organic compound having 2 hydroxyl groups or a simple derivative thereof. The diol may be substituted with one or more functional groups such as halogen, ether, thioether, and oxo (keto) which do not substantially interfere with the various reactions described in the processes herein. The diol may include an aromatic ring as part of its structure.

By "monomer" is meant a dicarboxylic acid, hydroxy carboxylic acid, or diol, as defined above.

By a "cyclic ester oligomer" (CEO) is meant a cyclic compound that is derived from at least one dicarboxylic acid and at least one diol, at least one hydroxycarboxylic acid, or a combination of at least one dicarboxylic acid, at least one diol, and at least one hydroxycarboxylic acid. The various diol, dicarboxylic acid, and hydroxycarboxylic acid moieties in the CEO are connected by ester groups.

By a "dimeric" CEO herein is meant a compound derived from a dicarboxylic acid and diol that has two dicarboxylic acid moieties and two diol moieties present in the CEO, while if the dimeric CEO is made from a hydroxycarboxylic acid it is derived from two such molecules. Trimeric, tetrameric, etc. CEOs have analogous definitions. CEOs may be made from two more different dicarboxylic acids, two or more different diols, and/or two or more hydroxycarboxylic acids. CEOs will preferably have a degree of polymerization (DP) of about 1 to about 20, or preferably, about 1 to about 10, or more preferably, about 1 to about 5.

By a "linear ester oligomer" (LEO) herein is meant a linear compound derived from one or more dicarboxylic acids and one or more diols, one or more hydroxycarboxylic acids, or a combination of one or more dicarboxylic acids, one or more diols, and one or more hydroxycarboxylic acids. LEOs will preferably have a degree of polymerization (DP) of about 1 to about 20, or preferably, about 1 to about 10, or more preferably, about 1 to about 5.

LEOs may be made by melt polymerization; solution polymerization; enzyme-catalyzed polymerization; the depolymerization of polyesters, including the thermal depolymerization of polyesters and the alcoholysis (e.g. methanolysis) and hydrolysis of polyesters; or other methods known to those skilled in the art. For examples of the use of melt polymerization, see F. W. Billmeyer, *Textbook of Polymer Science*, 3$^{rd}$ Edition (1984), John Wiley & Sons, pp. 25–48. For examples of the use of depolymerization, see Shibata, Mitsuhiro, et al., "Depolymerization of poly(butylenes terephthalate) using high-temperature and high-pressure methanol", *J. Applied Polymer Science*, (2000), 77(14), 3228–3233. For examples of the use of enzyme catalysis, see Kumar, Rajesh, et al., "Enzymatic Synthesis of multicomponent copolymers and their structural characterization", *Polymer Preprints* (American Chemical Society, Division of Polymer Chemistry) (2003), 44(1), 998–999.

The term "linear ester oligomer" (LEO) also encompasses mixtures containing both at least one linear compound derived from one or more dicarboxylic acids and one or more diols, one or more hydroxycarboxylic acids, or a combination of one or more dicarboxylic acids, one or more diols, and one or more hydroxycarboxylic acids and CEOs that are naturally present when LEOs are formed by either polymerization or depolymerization in the presence of a transesterification catalyst. The amount of CEOs that will naturally be present is predicted by thermodynamic equilibrium, as taught by H. Jacobson and W. H. Stockmeyer in "Intermolecular Reaction and Polycondensation I. The Theory of Linear Systems", *The Journal of Chemical Physics*, Vol. 18 Number 12, December 1950.

One type of preferred diol from which the LEOs used in the invention are derived is an aliphatic diol, that is a diol in which each hydroxyl group is bound to different alkyl carbon atoms. Other preferred diols include diols of the general formula $HOCH_2(CR^1R^2)_nCH_2OH$, wherein $R^1$ and $R^2$ are each independently hydrogen or an alkyl group and n is an integer of 0 to 10, and preferably all $R^1$ and $R^2$ are hydrogen and especially preferably n is 0 or an integer of 1 to 4, and more preferably is n is 1 or 2. Also preferred are diols of the general formula $HO((CH_2)_pO)_rH$, where p is 2–15 and r is 1–10. More preferred are diols of the same general formula where p is 2–10 and r is 1–5. Also preferred are alicyclic diols such as cyclohexane dimethanol. Aromatic diols such as hydroquinone may be used, as may thioethers.

Preferred dicarboxylic acids (or their derivatives including half-acid esters and diesters) from which the LEOs used in the invention are derived are isophthalic acid, substituted isophthalic acids, terephthalic acid, substituted terephthalic acids, and 2,6-naphthalenedicarboxylic acid, and combinations thereof. More preferred carboxylic acids are terephthalic acid and isophthalic acid, and terephthalic acid is especially preferred. Preferred aliphatic dicarboxylic acids are adipic acid, glutaric acid, succinic acid, sebacic acid, and maleic acid. It is particularly preferred that the dicarboxylic acid used be in the form of a diester. Any combination of preferred dicarboxylic acid and the diols specified in the general formula above may be used to form a preferred LEO for use in the present invention.

Preferred combinations of dicarboxylic acids and diols from which the LEOs used in the invention are derived include dimethyl terephthalate with ethylene glycol, 1,3-propanediol, 1,4-butanediol, di(ethylene glycol), di(butylene glycol), di(propylene glycol), tri(butylene glycol), or mixtures thereof; dimethyl isophthalate with ethylene glycol, 1,3-propanediol, or 1,4-butanediol di(ethylene glycol), di(butylene glycol), di(propylene glycol), tri(butylene glycol), or mixtures thereof; dimethyl terephthalate with cyclohexane dimethanol; and dimethyl 2,6-naphthalenedicarboxylate with ethylene glycol, 1,3-propanediol, 1,4-butanediol, di(ethylene glycol), di(butylene glycol), di(propylene glycol), tri(butylene glycol), or mixtures thereof.

When used, hydroxycarboxylic acids such as p-hydroxybenzoic acid and 2-hydroxyl-6-naphthoic acid will preferably be used as comonomers with diols and dicarboxylic acid.

It will be clear that the CEOs formed in the process of the invention will also preferably be formed from the foregoing diols and dicarboxylic acids (or their derivatives including half-acid esters and diesters).

In the process of the present invention LEOs dissolved in a solvent are continuously converted to CEOs in an intramolecular cyclization reaction that is catalyzed by a transesterification/esterification enzyme. The CEOs thus formed are removed from contact with the enzyme, isolated, and collected. Unreacted LEOs are continuously brought back into the presence of the enzyme and are further continuously converted to CEOs. The LEOs used in the process may be made prior to being introduced to the process by any method known to those skilled in the art, such as those listed above. The LEOs may also be made in situ during the process of the present invention. LEOs that are made in situ will preferably be made by the enzyme-catalyzed reaction of dicarboxylic acid and diol and/or hydroxycarboxylic acid monomers. The enzyme used for this reaction may be the same enzyme that is used to convert LEOs to CEOs or may be a different enzyme. Alternatively, LEOs may be both made prior to being introduced to the process of the invention and made in situ from monomers during the process. LEOs may also be generated during the process by the reaction of pre-made LEOs with additional monomers to form LEOs with higher degrees of polymerization. The CEOs formed by the enzyme catalyzed reaction of LEOs may have lower DP's than the LEOs they were formed from. When this is the case, the enzyme-catalyzed intramolecular cyclization of an LEO will generate another LEO or a diol, dicarboxylic acid, or hydroxycarboxylic acid as a byproduct.

In the process of the present invention, reactants (the term "reactants" when used herein refers to LEOs and/or monomers), are dissolved in an organic reaction solvent to prepare a reaction mixture. If necessary, the solvent may be heated to dissolve the reactants. Preferred solvents include toluene, tetrahydrofuran, o-dichlorobenzene, hexane, diphenyl ether, methyl isobutyl ketone, methyl ethyl ketone, or mixtures thereof. More preferred are toluene, o-dichlorobenzene, and methyl isobutyl ketone.

The enzyme used in the present reaction is at least one enzyme that can catalyze the esterification of carboxylic acids, the transesterification of esters, and/or the hydrolysis of esters. Typical types of enzymes that may be used include lipases, proteases, and esterases. For example see the chapter R. J. Kazlaukas, et al., "Biotransformation with Lipases," in *Biotechnology*, $2^{nd}$ Ed, Vol. 8a, Eds. H. J. Rehm et al., Wiley-VCH, Weinheim, Germany, p. 40–191 (1998). The enzyme is not soluble in the reaction mixture and may be attached to a solid material (supported or immobilized); see for instance G. E. Bickerstaff, Ed., *Immobilization of Enzymes and Cells*, Humana Press, Totowa, N.J., 1997. Supports may include materials such as diatomaceous earth, polysaccharides (e.g., chitosan, alginate or carrageenan), titania, silica, alumina, polyacrylates and polymethacrylates, and ion exchange resins, and the enzyme may be adsorbed, covalently attached, or ionically attached, or in the form of crosslinked enzyme crystals (CLECS). The enzyme may also be used without prior immobilization on a support and may be suspended in the stirred reaction mixture. The specific activity of the immobilized enzyme is preferably about 0.1 lU/g immobilized enzyme to about 2000 lU/g immobilized enzyme, more preferably about 10 lU/g immobilized enzyme to about 500 lU/g of immobilized enzyme.

Preferred enzymes for use in the present invention are bacterial and fungal enzyme catalysts that are derived from organisms of the genera *Aspergillus, Arthrobacter, Alcaligenes, Bacillus, Brevibacterium, Pseudomonas, Chromobacterium, Candida, Fusarium, Geotrichum, Humicola, Mucor, Pichia, Penicillium, Rhizomucor, Rhizopus* or *Thermus*. Particularly preferred bacterial and fungal enzyme catalysts are derived from the genera and species *Arthrobacter* sp., *Alcaligenes* sp., *Aspergillus niger, Aspergillus oryzae, Bacillus cereus, Bacillus licheniformis, Bacillus subtilis, Bacillus coagulans, Brevibacterium ammoniagenes, Burkholderia plantarii, Candida antartica, Candida cylindracea, Candidia lipolytica, Candida utilis, Candida rugosa, Chromobacterium viscosum, Fusarium solani, Geotrichum candidum, Humicola lanuginosa, Mucor* sp., *Mucor japonicus, Mucor javanicum, Mucor miehei, Pichia miso, Rhizomucor miehei, Rhizopus* sp., *Rhizopus nigricans, Rhizopus oryzae, Rhizopus arrhizus, Rhizopus delemar, Rhizopus niveus, Penicillium acylase, Penicillium roqueforti, Thermus aquaticus, Thermus flavus, Thermus thermophilus, Chromobacterium viscosum, Pseudomonas* sp., *Pseudomonas aeruginosa, Pseudomonas burkholderia, Pseudomonas cepacia, Pseudomonas fluorescens* or *Pseudomonas putida*. The most preferred lipases are derived from *Candida antartica*, such as *Candida antartica* B-lipase "CALB" (Anderson et al., *Biocatalysis and Biotransformation*, 16:181–204 (1998)). Examples of suitable, commercially-available, catalysts derived from *C. antartica* include, but are not limited to, Novozym® 435 (Product # L4777, Sigma-Aldrich, Mo.) and CHIRAZYME L-2, c-f C2, lyo (ID# 2207257, Biocatalytics, Pasadena, Calif.).

Throughout the process, enough water must be present in the reaction mixture to keep the enzyme hydrated and in an catalytically active state. A suitable amount of water may need to be added to the solvent at the beginning of the process, and it is often necessary to continue to add water throughout the process. The amount of water present throughout the reaction that is required to maintain the enzyme activity can be determined by measuring the rate of production of CEOs. For methods of assaying enzyme activity, see: J. Anderson, T. Byrne, K. J. Woelfel, J. E. Meany, G. T. Spyridis, Y. Pocker *Journal of Chemical Education*, vol. 71, 715–718 (1994); T. Furutani, R. Su, H. Ooshima, J. Kato *Enzyme and Microbial Technology*, vol. 17, 1067–1072 (1995); and J. Zhou, R. J. Ain, C. M. Riley, R. L. Schowen *Analytical Biochemistry*, vol. 231, 265–267 (1995). Generally, the more hydrophilic the solvent, the more water must be added. For example, when hexane is used as the solvent, about 50 ppm of water is required. When toluene is used, about 100 to about 200 ppm of water is needed and when methyl isobutyl ketone is used, about 400–500 ppm of water should be present. The water level present in the solvent can be determined using Karl-Fischer titration or other methods known to those skilled in the art.

The reaction mixture is preferably continuously purged during the process, preferably with an inert gas, to remove the byproducts of the transesterification/esterification process, such as any alcohols that are formed. The purging process may also remove water, requiring that water levels be maintained by the addition of water throughout the process in order to maintain enzyme activity. If the purging process removes solvent, additional solvent may have to be added throughout the process as well.

The process of the present invention comprises continually contacting LEOs with the enzyme in a reaction vessel under conditions in which the reactants will be partially or fully converted to CEOs. The enzyme may be attached to a solid support, or used unsupported. It may be present as a fixed bed or may be suspended in the stirred reaction mixture and the reaction vessel will be maintained at a temperature (the "reaction temperature") at which the enzyme will catalyze the formation of CEOs from LEOs. The reaction mixture is continuously fed to a separation apparatus where all or a portion of the CEOs formed are, using any method known to those skilled in the art, removed and, if necessary, purified. By separation apparatus is meant any vessel or other apparatus, such as a filter, extractor, etc. in which CEOs are removed from the reaction mixture. The remaining reaction mixture depleted in CEOs is then continuously brought back into contact with the enzyme. Additional LEOs and/or monomers may be added to the reaction mixture before or when it is brought back into contact with the enzyme in a reaction vessel. At least a portion of added monomers will react, catalyzed by the enzyme, to generate LEOs. Monomers present may also react with LEOs already present to generate LEOs with a higher degree of polymerization. When there is more diol than dicarboxylic acid present, or vice versa, the monomers may also react with LEOs to lower the degree of polymerization of the LEOs. It is preferable to add excess diol or excess dicarboxylic acid monomer to the reaction mixture in order to reduce the degree of polymerization of LEOs present. This is desirable when LEOs with lower degrees of polymerization are more soluble in the reaction solvent than those with higher degrees of polymerization. The CEOs formed will preferably have a degree of polymerization of 2 to about 30, or more preferably 2 to about 10. The enzyme continuously catalyzes the conversion of all or a portion of LEOs present to CEOs.

Any suitable method may be used in a separation apparatus to remove CEOs from the reaction mixture. If CEOs and the rest of the reaction mixture (e.g., LEOs and monomers, if any) have different solubilities in the reaction solvent at temperatures below the reaction temperature, when removed from the enzyme, the reaction mixture is fed to a vessel that is maintained at a temperature at which either the CEOs formed in the reaction or the LEOs and monomers are at least partially insoluble and where at least a portion of them precipitate out of solution. In the former case, the insoluble, precipitated CEOs are removed from the process and collected by any suitable means, such as filtration, and the resulting CEO-depleted reaction mixture is continuously brought back into contact with the enzyme at the reaction temperature. In the latter case, the CEO-containing solution is removed from the vessel and the CEOs are collected by any suitable means. Examples of methods of isolating CEOs include: removal of the solvent by evaporation or distillation; adding a cosolvent to precipitate the CEOs and collecting the precipitate; and extracting the CEOs into another solvent and isolating them from that solvent by precipitation or removal of the second solvent by evaporation or distillation. Any insoluble, precipitated LEOs are collected by any appropriate method, such as by using a continuous rotary filter and are redissolved in the reaction solvent and brought back into contact with the enzyme at the reaction temperature.

Another method is applicable where the CEOs and the LEOs and any monomers present have different solubilities in a solvent that is not miscible with the reaction solvent. In this method, some or all of the CEOs or LEOs and monomers are removed from the reaction mixture by counter-current extraction with the non-miscible solvent. In the case where CEOs are soluble in the non-miscible solvent, this solvent stream is removed from the process and the extracted CEOs are collected by any suitable means, such as precipitation, extraction, evaporation, and crystallization, while the remainder of the reaction mixture is brought back into contact with the enzyme at the reaction temperature. In the case where LEOs and monomers are soluble in the non-miscible solvent, the solution containing the CEOs is removed from the process and the CEOs are isolated. The extracted LEOs and monomers are brought back into contact with the enzyme at the reaction temperature. They may be subjected to a second counter-current extraction with the reaction solvent, the extracted solution may be diluted with the reaction solvent, or the non-miscible solvent may be removed and the isolated LEOs and monomers may be redissolved in the reaction solvent before they are brought back into contact with the enzyme.

In another method of removing CEOs from the reaction mixture, an additional solvent that causes either some or all of the CEOs or some or all of the LEOs and monomers present to precipitate from solution is added. In the latter case, the CEO-enriched solution is removed and the CEOs are collected. The insoluble LEOs and monomers are collected by any appropriate method, such as by using a continuous rotary filter, and are redissolved in the reaction solvent and brought back into contact with the enzyme. In the former case, the insoluble CEOs are removed from the process and collected and the remaining LEOs and monomers are brought back into contact with the enzyme, after removing them from the second solvent by any suitable method such as counter-current extraction, evaporation, crystallization, and redissolution, or dilution with the reaction solvent.

In another method of removing CEOs from the reaction mixture, all of the components are removed from solution by a method such as cooling, the addition of an anti-solvent, evaporation of the solvent, or other method known to those skilled in the art. CEOs are isolated by crystallization, melt crystallization, or the addition of a solvent in which either CEOs or LEOs and monomers are soluble at the temperature used.

CEOs may also be removed from the reaction mixture or other solution containing LEOs and monomers by other means such as selective crystallization; passing the solution through a semi-permeable membrane; a distillation technique such as short-path distillation; sublimation; using an adsorbant selective for CEOs or LEOs and monomers; or other methods known to those skilled in the art.

It is not necessary to isolate all of the CEOs from the reaction mixture when using the foregoing methods. CEOs remaining with LEOs and monomers are brought back into contact with the enzyme and can react further or can be isolated later in the process. The purity of the CEOs collected from the process of the present invention will be at least 50 percent by weight, or preferably at least 75 percent by weight, or more preferably, at least 90 percent by weight. Impurities may comprise LEOs and/or monomers. The CEOs may be further purified by any known purification technique such as chromatography or recrystallization.

One embodiment of the continuous process of the present invention uses a recirculating reactor. An initial reaction mixture is brought into contact with the enzyme in a reaction vessel. This initial reaction mixture comprises a solution of any of the reactants used in the present invention. The reaction vessel is maintained at a temperature at which all components of the initial reaction mixture as well as any LEOs and CEOs that are formed in the course of the reaction are soluble. The reaction vessel is preferably continuously stirred. The enzyme catalyzes the esterification/transesterification of the reactants to generate a reaction mixture enriched in CEOs. The reaction mixture from the reaction vessel is removed from contact with the enzyme by any known method, such as continuous filtration, extraction, Soxhlet extraction, centrifugation, etc., and is continuously fed to a separation apparatus, which may also be a continuously stirred vessel. CEOs are removed from the reaction mixture in the separation apparatus using a method such as one of those described above and the resulting reaction mixture depleted in CEOs is returned to the reaction vessel where it is brought back into contact with the enzyme and where further reaction occurs. Additional reaction mixture may be added throughout the process to replenish the amounts of reactants present.

The reaction mixture may be transferred between the reaction vessel and separation apparatus by tubing, piping or other means that permits liquid transport. The reaction mixture may be pumped or gravity fed between the reaction vessel and separation apparatus and additional vessels and apparatus may be included in the loop.

A second embodiment of the present invention uses a linear reactor that comprises a plurality of reaction vessels/separation apparatus connected in series. An initial reaction mixture is brought into contact with the enzyme in a first reaction vessel. This initial reaction mixture may comprise a solution of any combination of reactants capable of reacting to form CEOs in the presence of the enzyme. The first reaction vessel is maintained at a temperature at which all components of the initial reaction mixture as well as any LEOs and CEOs that are formed in the course of the reaction are soluble. The first vessel is preferably continuously stirred. The enzyme catalyzes the esterification/transesterification of the reactants to generate a reaction mixture enriched in CEOs. The reaction mixture from the first reaction vessel is removed from contact with the enzyme and is continuously fed to a first separation apparatus.

CEOs are removed from the reaction mixture in the separation apparatus using a method such one of those described above and the resulting reaction mixture depleted in CEOs is optionally continuously passed to a second reaction vessel that is maintained at a temperature at which all components of the reaction mixture are soluble and which contains the enzyme. The reaction mixture in turn is optionally continuously fed to a second separation apparatus in which CEOs are removed from the process. As many reaction vessels and separation apparatus as desired may be linked in this fashion, where the reaction mixture is continuously fed from a reaction vessel containing enzyme to a separation apparatus containing no enzyme and in which CEOs are removed. The number of reaction vessels and separation apparatus used will depend on the degree of conversion of reactants or amount of product desired. It is not necessary that the method of separation of the CEOs from the reaction mixture be the same in each separation apparatus.

Additional reaction mixture may be added throughout the process to replenish the amounts of reactants present. The reaction mixture may be transferred between the reaction vessels and separation apparatus by tubing, piping or other means that permits liquid transport. The reaction mixture may be pumped or gravity fed between the reaction vessels and separation apparatus and additional vessels and apparatus may be included in the series.

The second embodiment is preferred over the first when the LEOs are less soluble than the CEOs in the reaction solvent at temperatures below the reaction temperature.

Preferred CEOs formed by the process of this invention are the dimer derived from 1,4-butanediol and dimethyl terephthalate (3,8,15,20-tetraoxatricyclo[20.2.2.210,13]octacosa-10,12,22,24,25,27-hexaene-2,9,14,21-tetrone) (structure 1); the trimer formed from 1,4-butanediol and dimethyl terephthalate (3,8,15,20,27,32-hexaoxatetracyclo[32.2.2.210,13.222,25]dotetraconta-10,12,22,24,34,36,37,39,41-nonaene-2,9,14,21,26,33-hexone); the dimer formed from 1,3-propanediol and dimethyl terephthalate (3,7,14,18-tetraoxatricyclo[18.2.2.29,12]hexacosa-9,11,20,22,23,25-hexaene-2,8,13,19-tetrone) (structure 2); the dimer formed from di(ethylene glycol) and dimethyl terephthalate (3,6,9, 16,19,22-hexaoxatricyclo[22.2.2.211,14]triaconta-11,13,24,26,27,29-hexaene-2,10,15,23-tetrone)(structure 3); and the trimer formed from ethylene glycol and dimethyl terephthalate (3,6,13,16,23,26-hexaoxatetracyclo[ 26.2.2.28,11.218,21]hexatriaconta-8,10,18,20,28,30,31,33,35-nonaene-2,7,12,17,22,27-hexone

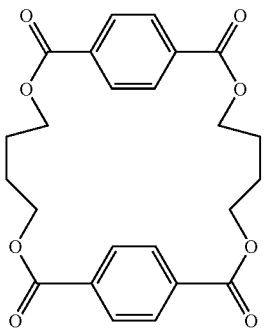

1

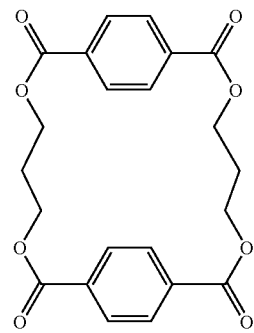

2

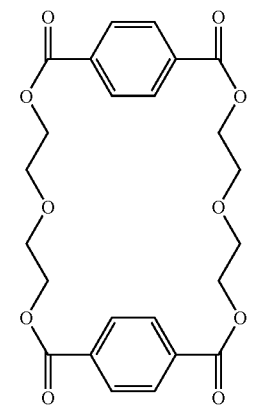

3

The CEOs formed by the process of the present invention may be polymerized to higher molecular weight polyesters, which have many applications in injection molding, blow molding, extrusion molding, fibers, filaments, and films and are useful for making durable and disposable goods. The CEOs may also be polymerized directly in a mold.

EXAMPLES

Example

A schematic diagram of the reactor used is shown in FIG. 1. 10 is a 600 mL jacketed reaction vessel containing Chirazyme® L-2 lipase supported on polymer beads, and a 0.1 M solution of dimethyl terephthalate and di(ethylene glycol) in toluene. 11 is a 600 mL reaction vessel that is maintained at room temperature. Each reactor is equipped with running stirrers 12. The temperature of the solvent in vessel 10 is maintained at 50–55° C. using hot silicone oil that is heated by heater 14 and circulated through jacket 15 of vessel 10. The reaction solution is pumped by pump 16 into vessel 11 via tubing 17, the lipase being held in place by fritted glass filter 13. The desired CEO product of the reaction, the cyclic dimer derived from dimethyl terephthalate and di(ethylene glycol) (CPEOT) (structure 3), precipitates out in vessel 11 and is collected on fritted filter 18. The filtered, room-temperature reaction solution is pumped by pump 19 to the top of vessel 10 through tubing 20. Meanwhile, sufficient dimethyl terephthalate and di(ethylene glycol) dissolved in toluene is added to the top of vessel 10 via opening 21 to maintain the concentration of starting materials in vessel 10 as well as a constant volume. The reaction solution is continuously purged with a 50 mL/min nitrogen flow and 1 μl/min of water is continuously added. The reaction is run continuously as long as desired. At the completion of the reaction, vessel 11 is emptied and the collected CPEOT is collected. Its purity is greater than 90% as measured by HPLC and can be further purified by column chromatography on silica gel.

Samples are analyzed by LCMS using the following technique. Approximately 10 drops of the reaction mixture are placed in 1.5 ml of o-cresol. The o-cresol mixture is heated at 100 to 125° C. for 5 min, with stirring. Then, 5 drops of the o-cresol solution are added to 3 ml of chloroform and the mixture is shaken and filtered through a 0.45 micron filter (Acrodisc® CR 25 mm syringe filter, Gelman Laboratory) into a liquid chromatograph sample vial. Analysis is carried out using a Hewlett-Packard® 1100 Liquid Chromatograph equipped with a HP G1315A UV Diode array detector and a HP G1946A Mass Spectrometer detector. Two PLGel® 50 Angstrom columns are utilized with $CHCl_3$ as the eluant at a rate of 1 ml/min. Cyclic oligomer peaks are identified via mass chromatographic spectrum and, where available, samples of pure cyclic oligomer extracted from the corresponding high molecular weight polymer. Concentrations of cyclic oligomers are determined via uncorrected area percent calculations.

What is claimed is:

1. A process for the production of cyclic ester oligomers, comprising carrying out in a continuous manner the steps of:
    (iii) contacting linear ester oligomers, having a degree of polymerization of about 1 to about 20, dissolved in a solvent with an enzyme to generate a solution enriched in cyclic ester oligomers, and
    (iv) separating the cyclic ester oligomers from the solution.

2. The process of claim 1 wherein a recirculating reactor is used to produce the cyclic ester oligomers.

3. The process of claim 1 wherein a linear reactor is used to produce the cyclic ester oligomers.

4. The process of claim 1 wherein the linear ester oligomers are derived from diols of the formula $HO((CH_2)_pO)_rH$, where p is 2–10 and r is 1–5, and dimethyl terephthalate.

5. The process of claim 1 wherein the linear ester oligomers are derived from diols of the formula $HO((CH_2)_pO)_rH$, where p is 2–15 and r is 1–10, and dimethyl terephthalate.

6. The process of claim 1 wherein the enzyme is at least one lipase, protease, and/or esterase.

7. The process of claim 1 wherein the cyclic ester oligomers are separated from the solution by precipitation.

8. The process of claim 1 wherein the cyclic ester oligomers are separated from the solution by extraction.

9. The process of claim 1 where the cyclic ester oligomers are separated from the solution by evaporation.

10. The process of claim 1 where the cyclic ester oligomers are separated from the solution by crystallization.

* * * * *